(12) United States Patent
Hiriyannaiah

(10) Patent No.: US 9,194,941 B2
(45) Date of Patent: *Nov. 24, 2015

(54) ULTRASOUND IMAGE ENHANCEMENT AND SUPER-RESOLUTION

(71) Applicant: eagleyemed, Inc., Santa Clara, CA (US)

(72) Inventor: Harish P. Hiriyannaiah, San Jose, CA (US)

(73) Assignee: Eagleyemed Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/564,954

(22) Filed: Dec. 9, 2014

(65) Prior Publication Data

US 2015/0092515 A1 Apr. 2, 2015

Related U.S. Application Data

(63) Continuation of application No. 14/292,431, filed on May 30, 2014.

(60) Provisional application No. 61/829,894, filed on May 31, 2013.

(51) Int. Cl.
G01S 15/00 (2006.01)
G10K 11/00 (2006.01)
G01S 7/52 (2006.01)
G10K 11/34 (2006.01)
B06B 1/02 (2006.01)
G01S 15/02 (2006.01)
G10K 11/26 (2006.01)

(52) U.S. Cl.
CPC ............ *G01S 7/52017* (2013.01); *B06B 1/0215* (2013.01); *G01S 7/5202* (2013.01); *G01S 7/5208* (2013.01); *G01S 7/52034* (2013.01); *G01S 7/52047* (2013.01); *G01S 7/52085* (2013.01); *G01S 15/02* (2013.01); *G10K 11/26* (2013.01); *G10K 11/341* (2013.01)

(58) Field of Classification Search
USPC .............................................. 367/7
See application file for complete search history.

(56) References Cited

U.S. PATENT DOCUMENTS

| | | | | |
|---|---|---|---|---|
| 5,940,123 | A | 8/1999 | Daigle et al. | |
| 6,014,473 | A * | 1/2000 | Hossack et al. | 382/294 |
| 6,102,865 | A * | 8/2000 | Hossack et al. | 600/459 |
| 6,132,376 | A * | 10/2000 | Hossack et al. | 600/443 |
| 6,186,949 | B1 * | 2/2001 | Hatfield et al. | 600/443 |
| 6,201,900 | B1 * | 3/2001 | Hossack et al. | 382/294 |
| 6,222,948 | B1 * | 4/2001 | Hossack et al. | 382/294 |
| 6,360,027 | B1 * | 3/2002 | Hossack et al. | 382/294 |
| 8,914,245 | B2 * | 12/2014 | Hopkins | 702/56 |

(Continued)

OTHER PUBLICATIONS

International Search Report dated Apr. 6, 2015 from International Application No. PCT/US 14/40384.

(Continued)

*Primary Examiner* — James Hulka
(74) *Attorney, Agent, or Firm* — Beyer Law Group LLP

(57) ABSTRACT

Techniques to improve resolution in an ultrasound system are disclosed. An exemplary apparatus is a portable ultrasound probe having transducer elements and supporting electronics within the probe. The beam is shaped to split the resolution to sub-pixel accuracy. Super resolution sample technique based on interpolation can be used to further increase resolution. In one embodiment the ultrasound system supports ½ crystal physical resolution and ¼ crystal digital resolution.

30 Claims, 6 Drawing Sheets

(56) References Cited

U.S. PATENT DOCUMENTS

| | | |
|---|---|---|
| 2004/0092820 A1* | 5/2004 | Reinhardt et al. ............ 600/458 |
| 2005/0242183 A1 | 11/2005 | Bremer |
| 2007/0239001 A1 | 10/2007 | Mehi et al. |
| 2007/0282200 A1* | 12/2007 | Johnson et al. ............... 600/437 |
| 2008/0110263 A1* | 5/2008 | Klessel et al. ................. 73/602 |
| 2009/0271146 A1* | 10/2009 | Ammar ......................... 702/155 |
| 2010/0278008 A1* | 11/2010 | Ammar ............................. 367/7 |
| 2011/0320143 A1* | 12/2011 | Hopkins ........................ 702/56 |
| 2014/0276069 A1 | 9/2014 | Amble et al. |
| 2014/0355377 A1 | 12/2014 | Hiriyannaiah |

OTHER PUBLICATIONS

Written Opinion dated Apr. 6, 2015 from International Application No. PCT/US 14/40384.

U.S. Office Action dated Mar. 10, 2015 from U.S. Appl. No. 14/292,431.

\* cited by examiner

ULTRASOUND IMAGE ENHANCEMENT AND SUPER-RESOLUTION

CROSS REFERENCE TO RELATED APPLICATIONS

The present application is a Continuation of U.S. application Ser. No. 14/292,431, filed on May 30, 2014, which claims the benefit of U.S. Provisional Application No. 61/829,894, filed on May 31, 2013, the contents of both are hereby incorporated by reference.

This application incorporates by reference commonly owned U.S. patent application Ser. No. 14/214,370, entitled "Ultrasound Probe", filed on Mar. 14, 2014.

FIELD OF THE INVENTION

The present invention is generally related to improving image quality in ultrasound imaging systems. More particularly, the present invention is directed to achieving high image quality in an ultrasound system have a reduced number of transducer elements using super-sampling and intelligent scan line conversion.

BACKGROUND OF THE INVENTION

Ultrasound imaging machines include a transducer probe that includes piezoelectric crystals to generate sound waves and also detect the reflected waves. In a conventional ultrasound machine the transducer probe is connected to an external processing box by a cable, where the external processing box has electronics to generate high frequency voltage pulses sent to the transducer probe, receive detected signals from the transducer probe, and perform signal processing and scan line conversion to reconstruct the image.

Referring to FIG. 1, in a conventional ultrasound imaging machine the cable is typically several meters long (e.g., 2 m) and contains 48 to 256 micro-coaxial cables, where the number of micro-coaxial cables scales with the number of transducer elements in the transducer probe. The micro-coaxial cables are expensive and have other disadvantages. In particular, the micro-coaxial cables introduce a cable loss and a cable impedance. For example, a conventional 2 m cable might have a capacitance of 203 pF, while a transducer element could have a capacitance on the order of 5 pF. Additionally, a 2 m cable may introduce a 2 dB attenuation. The cable introduces a large capacitive loading, which makes it impractical to perform fine grained apodization of the transmitted voltage pulses sent to the transducer probe.

In ultrasound systems the spatial resolution of the image is determined by the size of the piezoelectric crystal ("crystal") elements of the transducers and the number of such crystal elements. Higher resolution typically implies smaller crystals and larger crystal arrays. Larger crystal arrays lead to more expensive systems and limitations on the physical layout and cabling of the system. In particular, the number of micro-coaxial cables required increases with the number of crystal elements. Thus, in the prior art increasing spatial resolution requires more crystal elements and more complex and costly cables.

Thus, ultrasound imaging systems are more expensive than desired. This is due, in part, to need for a large number of transducer crystals and the cost and complexity of the micro-coaxial cables and associated electronics. For example, in 2014 a commercial ultrasound imaging system may cost $30-50 k. Additionally, another problem in the prior art is that quality of the scan line processing to reconstruct the ultrasound image is poorer than desired. In particular, the scan line conversion at the distal end of the ultrasound beam results in poor resolution due to a lack of signal strength, loss of beam focus, and inadequate spatial binning.

The present invention was developed to address the above described problems in the prior art.

SUMMARY OF THE INVENTION

An apparatus, system, method, and non-transitory computer readable medium to provide super-resolution in an ultrasound image scanner is disclosed. The firing sequence of the transducer elements may be selected to achieve sub-pixel resolution, up to half crystal physical resolution. Additionally, interpolation may be used to achieve ¼ crystal digital resolution. The transducer elements, beam forming elements, scan conversion, and analog front end may be included within a handheld probe. The probe may also include auto-calibration and features to support fine temporal and spatial apodization. In a sector scanning embodiment, a zone-based interpolation technique may be used to selectively increase interpolation in regions with poor spatial binning.

DETAILED DESCRIPTION

Figure 1:
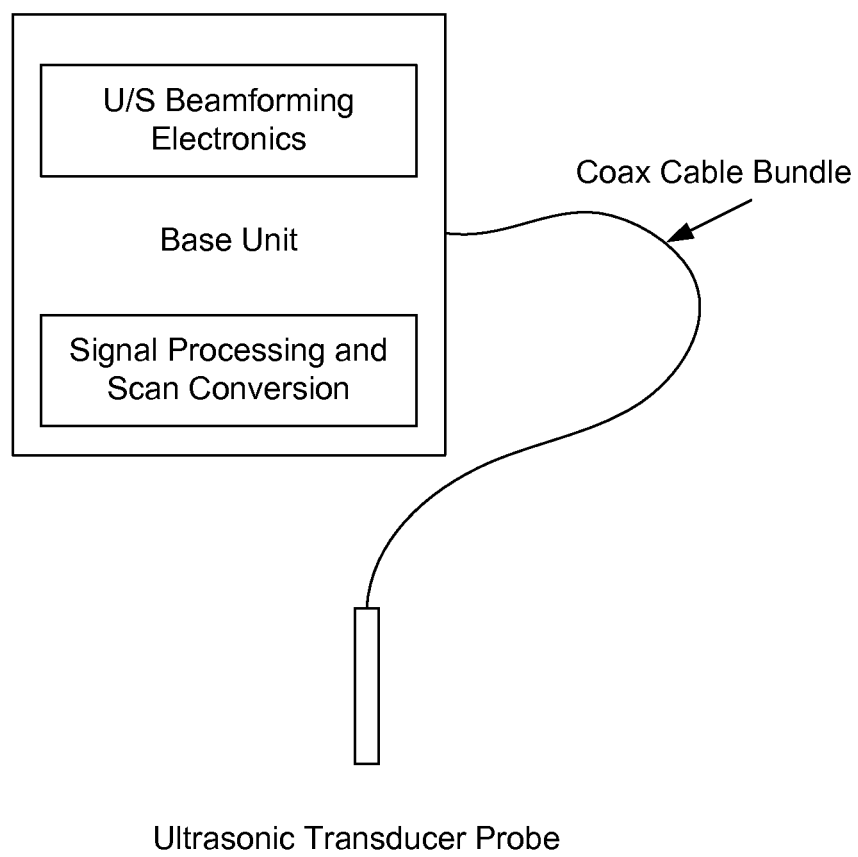
FIG. 1 illustrates a prior art ultrasound imaging system.
Figure 2:
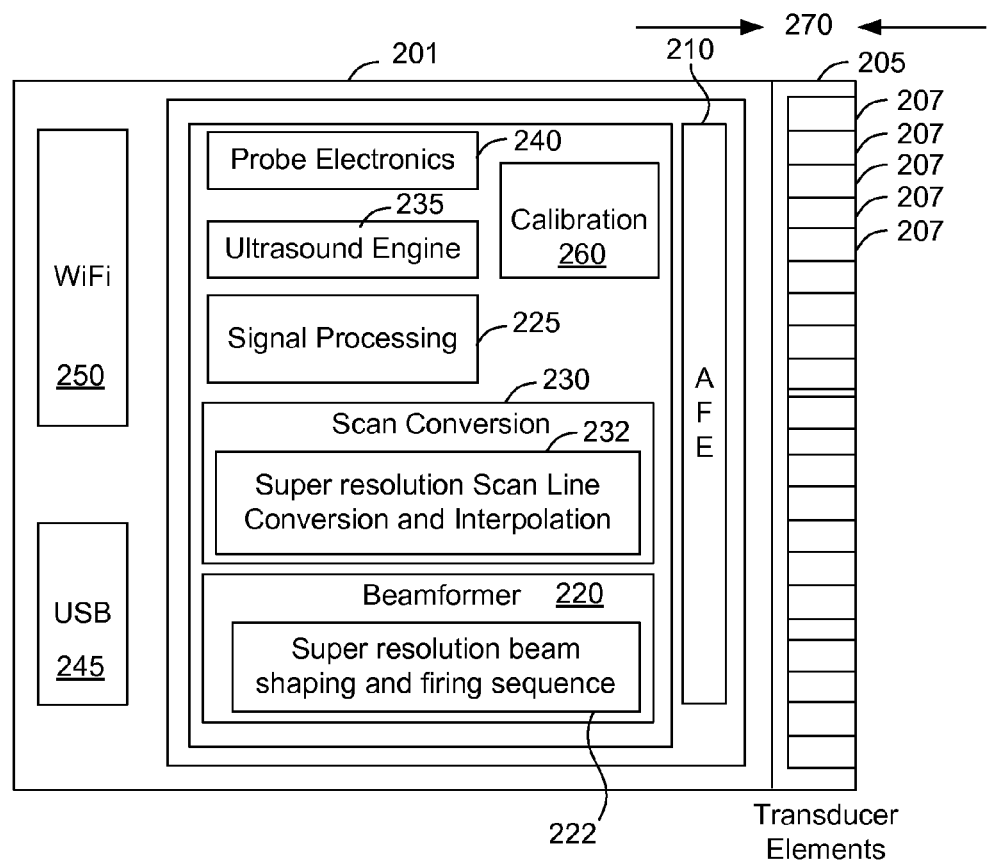
FIG. 2 illustrates an exemplary ultrasound probe in accordance with an embodiment of the present invention.

FIG. 2 illustrates an exemplary system in accordance with an embodiment of the present invention. A handheld probe has a housing 201 that contains a transducer array 205 having individual transducer elements 207, analog front end (AFE) 210, a beamformer 220, signal processing 225, scan conversion 230, ultrasound engine 235, and other probe electronics 240. The transducer array 205 includes an array of transducer elements 207, such as an array of piezoelectric crystals, to generate an ultrasound beam in a transmit mode and to detect reflected ultrasound signals in a receive mode.

In one embodiment the transducer elements are disposed in a detachable transducer head 270 that permits different transducer heads to be attached. This permits, for example, different geometric arrangements of the transducer elements and/or replacements for defective heads. A calibration module 260 provides auto-calibration of the probe in situ and supports replacing/substituting different transducer heads. The self-calibration of the array also allows superior control over the scanning process. In one embodiment the handheld probe supports linear array and sector scanning among other options.

The handheld probe also includes the analog and digital elements to generate the high voltage pulses for the transducer elements to generate ultrasound pulses. The digital electronics and analog front end 210 include voltage high voltage pulsers and delay elements permit the gain and delay of each high voltage pulser of the crystal segment to be precisely controlled. Additionally, the handheld probe includes signal processing electronics 225 to process the returned pulses and reconstruct the ultrasound image. The electronics and signal processing of the handheld probe also includes at least one processor (not shown) and associated memory.

The handheld probe supports scan conversion and outputs ultrasound images through either a wireless or wired connections, such as a USB port 245 or a wireless LAN connection 250. As all of the critical electronics are located within the probe there is no capacitive loading issues as in conventional ultrasound systems that use micro-coaxial cables to couple signals to and from the probe to an external processing box.

An individual transducer element 207 may be implemented as a piezoelectric crystal. In one embodiment the transducer array 205 has a short segment of crystals, such as 64 to 128, although more generally other numbers of crystal elements may be used. That is, the number of piezoelectric crystals is selected to be significantly less than the 128 to 256 elements in many conventional systems in order to reduce the size, cost, and complexity of the probe.

The handheld problem includes a module 222 to support super-resolution beam shaping and firing sequences. Module 222 may comprise hardware and software, such as digital waveform generators. In one embodiment a super-resolution mode in the spatial dimension is supported by selecting the gain and delay of pulses to the transducer array to achieve sub-crystal (i.e., sub-pixel resolution). Additional interpolation 232 may be provided in the software domain on a processor to further increase resolution when scan line conversion is preformed. This super-resolution thus provides at least a factor of two-to-four more samples, thus permitting a short segment of crystals (e.g., 64 to 128) to be used to obtain high resolution images.

Figure 3:
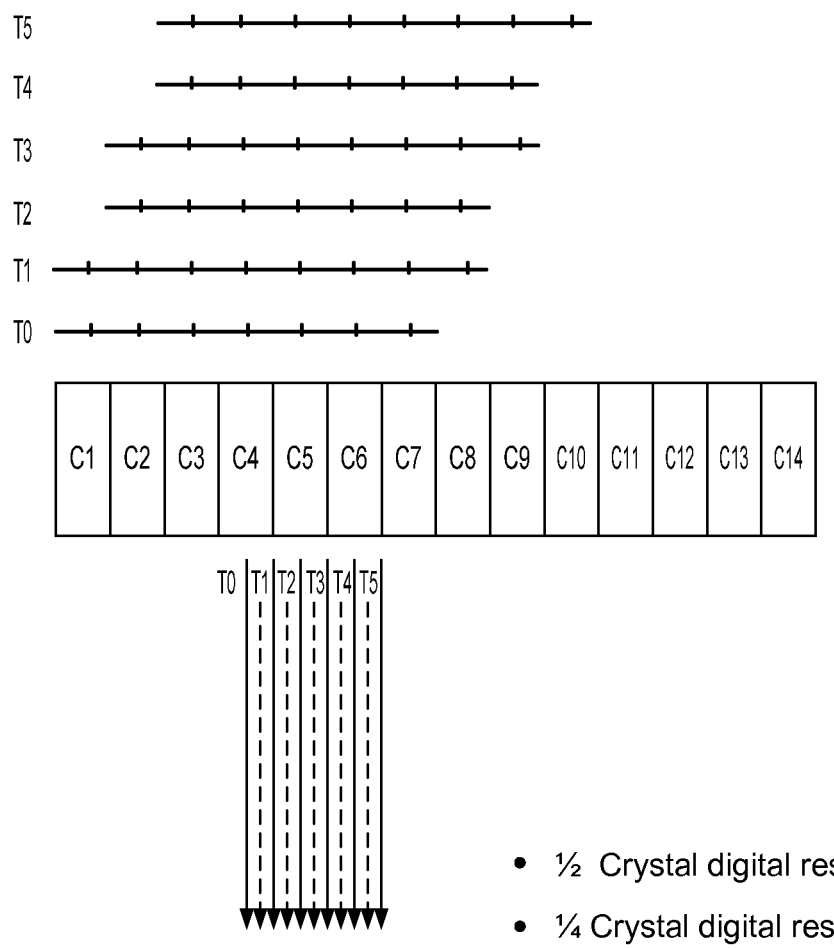
FIG. 3 illustrates a beam firing sequence in accordance with an embodiment of the present invention.

FIG. 3 illustrates aspects of a firing sequence for achieving sub-pixel resolution in accordance with an embodiment of the present invention. In one embodiment a select number of piezoelectric crystals are fired at a given time and translated in a sequence to move the transmitted beam focal point by ½ crystal (i.e., ½ pixel). As a result, the center of distribution of the pulse is shifted ½ crystal at a time in each firing sequence at T0, T1 . . . TN. This can include 1) varying the number of crystals driven in a particular firing cycle and 2) shifting the position of crystals activated. For example, FIG. 3 illustrates altering the firing cycle to have either 7 or 8 piezoelectric crystals active and also translating the distribution of active crystals that are fired. For example, at time T0, crystal elements C1 to C7 are fired, having a spatial distribution center at the middle of crystal C4. At time T1, crystals C1 to C8 are fired, shifting the center to the beginning of crystal C5. At time T2, crystals C2 to C9 are fired, shifting the center to the middle of crystal C5. As a result, in each transmit firing cycle the center of the pulse is shifted by ½ crystal resolution.

Additional interpolation may be used to achieve ¼ digital resolution (super-sample resolution), as indicated by the dashed lines. A variety of different interpolation techniques may be used to perform the digital interpolation, such as linear interpolation or other types of interpolation, such as higher order orthonormal interpolation or Fourier interpolation.

Figure 4A:
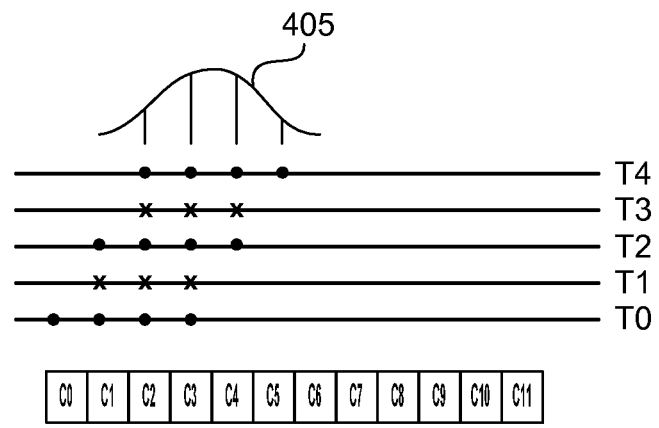
FIGS. 4A and 4B illustrates aspects of fine-grained temporal and spatial apodization in accordance with an embodiment of the present invention.
Figure 4B:
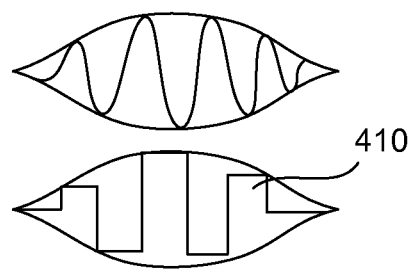

Referring to FIGS. 4A and 4B, in one embodiment the beam shaping has fine gained control of gain and beam shape. In one embodiment there is fine-grained spatial and temporal apodization may be performed. FIG. 4A illustrates that the gain may be controlled for each piezoelectric element in a firing sequence according to a gain profile 405. FIG. 4B illustrates that digital waveform generation techniques 410 may be used to approximate an ideal pulse waveform. That is, in one embodiment the apodization is fine grained in that there is that the control of the gain, bandwidth, and delay is less than 1%. This may include, for example, providing digital waveform generators to provides precise control of the transmit pulse waveforms for each individual crystal in the firing sequence and the use of highly accurate digital to analog converters (DACs), such as 14 bit or better DACs. In one embodiment the gain and delay of each HV pulser of the crystal segment is adjusted to obtain an effective beam shape that splits the resolution to a sub-pixel (sub-crystal) accuracy. This kind of beam forming also compensates for and improves beam focus on the transmission side. Similar time varying focus coefficients are employed on the receiving side to improve spatial focus.

Figure 5:
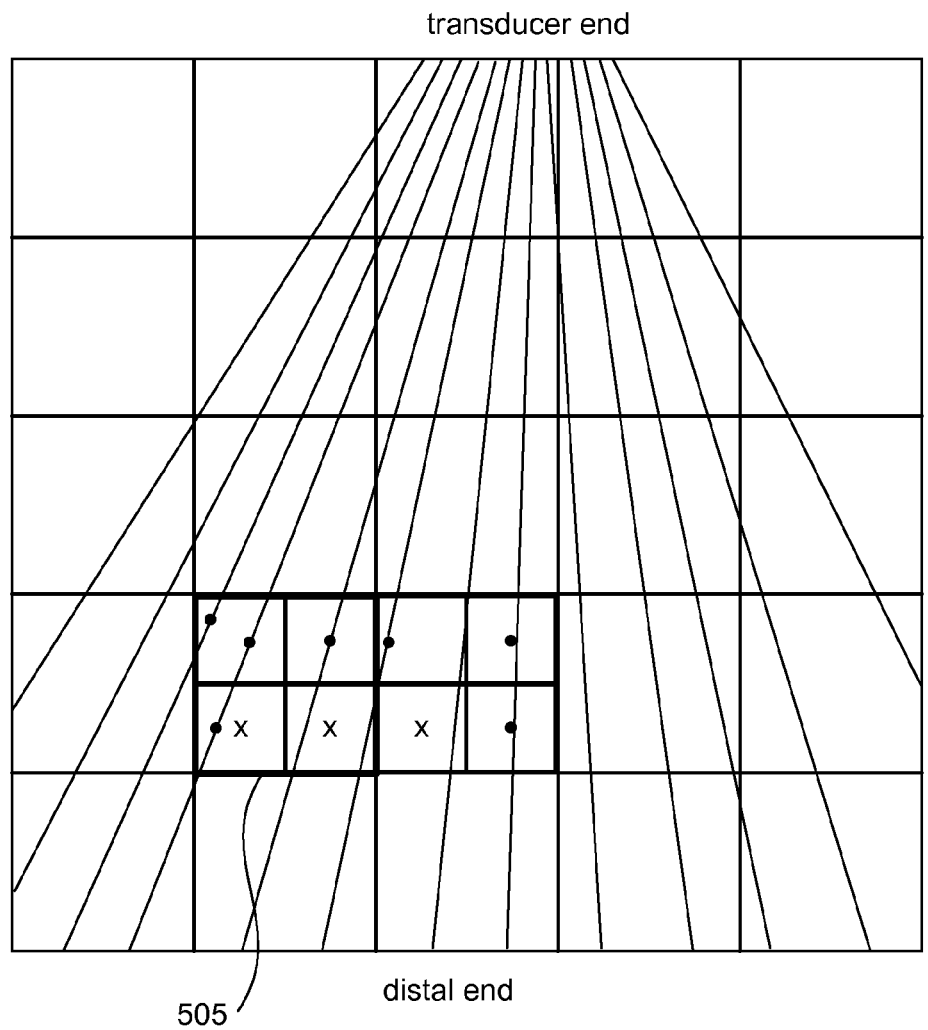
FIG. 5 illustrates scan line interpolation in accordance with an embodiment of the present invention.

FIG. 5 illustrates the use of interpolation to improve resolution by generating additional interpolated samples for the scan line processing sued to reconstruct the ultrasound imaging and obtain better spatial accuracy. FIG. 5 shows a sequence of scan lines in an image grid. Samples may be taken on scan lines and also on interpolated lines. Super-resolution sampling methods can be used to interpolate along the tangential direction (with respect to a scan line), to obtain better spatial accuracy. As illustrative examples, super-resolution sampling methods can include orthonormal expansion methods such as Legendre sampling, Tchebyshev sampling, Sinc sampling, or multirate interpolation.

Embodiments of the present invention may be applied to sector scanning. In one embodiment the amount of super-resolution is varied radially from the transducer, with more super-sampling at the distal end and very little at the transducer end. That is, in one embodiment the interpolation is performed in regions which traditionally have a lack of signal strength, loss of beam focus and inadequate spatial binning, as indicated in bin region 505, which illustrates the use of interpolation (dashed lines) to increase the number of samples, via interpolation from neighboring pixels. In regions distal to the transducer end the transmitted ultrasound beam may be spread out and the reflected beam highly attenuated. This improves scan-line conversion at the distal end of the beam which ordinarily suffers from problems such as lack of signal strength, loss of beam focus and inadequate spatial binning.

Figure 6:
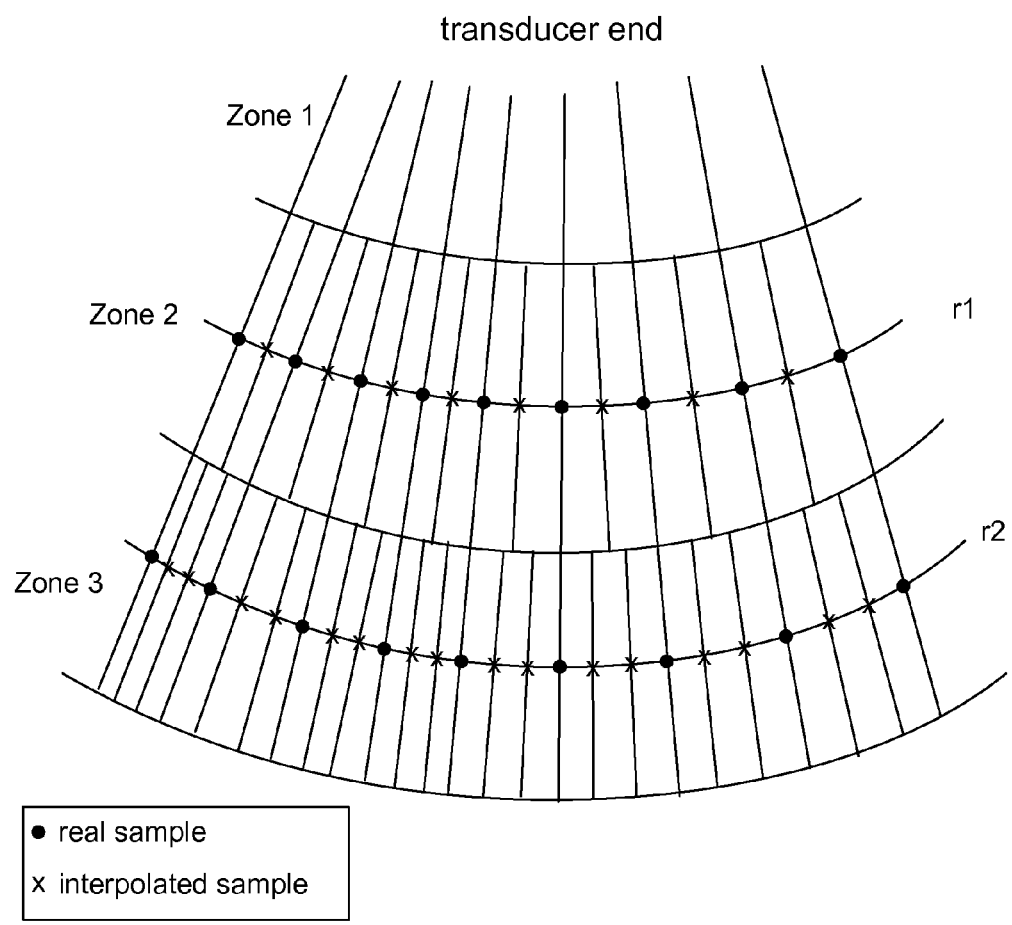
FIG. 6 illustrates scan line interpolation in a radial zone scheme in accordance with an embodiment of the present invention.

FIG. 6 illustrates a radial zone approach for performing interpolation in sector scanning. Three zones (Z1, Z2, Z3) are shown to illustrate principles of operation, although it will be understood that an arbitrary number of zones may be utilized. In a zone proximate the transducer end, such as zone 1, there is a high density of samples along the scan lines such that an individual pixel bin would have a number of samples. However, in radial zones further away from the transducer end, the density of real samples decreases and there is inadequate spatial binning of samples along the scan lines. Thus interpolation may be utilized selectively in zones farther away from the transducer end. For example, in zone 2, the samples along the scan line (solid dots) are illustrated along with interpolated sample (crosses) along radial line r1. In zones with even lower density of samples, such as zone 3, more aggressive interpolation may be used, in this case there is a further doubling of the amount of interpolation performed along radial line r2.

In one embodiment a user can select the type of binning utilized. That is, an individual pixel bin includes a number of samples along scan lines and interpolated samples. A gray scale (or color for color images) must be determined for the pixel. In one embodiment the options include an average, a median, a max, a min, a root mean square, or an arithmetic mean. This selection provides additional control for the clinician to adjust performance based on individual preferences. For example, selecting a "max" would ordinarily generate a more speckled image than selecting an "average."

While an exemplary apparatus has been described, additional details on an implementation of a portable ultrasonic probe is described in commonly owned U.S. patent application Ser. No. 14/214,370 "Ultrasound Probe", filed on Mar. 14, 2014, which is incorporated by reference.

While the invention has been described in conjunction with specific embodiments, it will be understood that it is not intended to limit the invention to the described embodiments. On the contrary, it is intended to cover alternatives, modifications, and equivalents as may be included within the spirit and scope of the invention as defined by the appended claims. The present invention may be practiced without some or all of these specific details. In addition, well known features may not have been described in detail to avoid unnecessarily obscuring the invention. In accordance with the present invention, the components, process steps, and/or data structures may be implemented using various types of operating systems, programming languages, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein. It will be understood that embodiments of methods of the present invention may also be tangibly embodied as a set of computer instructions stored on a computer readable medium, such as a memory device.

What is claimed is:

1. A method of providing super-resolution in an ultrasound imaging system having a handheld probe including piezoelectric transducer having an array of piezoelectric crystals, comprising:
   generating ultrasound pulses, including performing beam forming to generate voltage pulses within the handheld probe in a firing sequence in which a selection of active piezoelectric crystals is varied over time in a sequence selected to shift a spatial center of a transmitted ultrasound pulse over the firing sequence to achieve at least ½ piezoelectric transducer crystal physical resolution;
   detecting reflected ultrasound pulses within the handheld probe;
   performing scan conversion within the handheld probe; and
   outputting ultrasound image data via a digital interface.

2. The method of claim 1, wherein the firing sequence is selected to achieve ½ piezoelectric transducer crystal physical resolution and interpolation of detected reflected ultrasound pulses is performed to achieve ¼ piezoelectric crystal digital resolution.

3. The method of claim 1, wherein the selection of active piezoelectric crystals is varied by performing at least one of varying the number of piezoelectric crystals driven and shifting a position of piezoelectric crystals activated.

4. The method of claim 3, wherein the selection comprises sequentially varying a spatial distribution of active piezoelectric crystals to shift a transmitted beam focus by ½ piezoelectric transducer crystal physical resolution over the firing sequence.

5. The method of claim 4, further comprising performing interpolation in the scan conversion to increase a number of samples in scan line conversion.

6. The method of claim 1, wherein the selecting comprises varying a number of active piezoelectric crystals over the firing sequence.

7. The method of claim 1, wherein the selecting comprises varying a spatial distribution of active piezoelectric crystals over the firing sequence.

8. The method of claim 1, further comprising detecting reflected ultrasound pulses in the ultrasound probe with a sub-pixel resolution.

9. The method of claim 8, applying time varying focus coefficients for the detected ultrasound pulses to improve spatial focus.

10. The method of claim 1, wherein performing scan conversion includes performing scan line conversion of data received from reflected ultrasound pulses, including performing, in a scan line domain, interpolation of samples along a tangential direction.

11. The method of claim 10, wherein the interpolation comprises at least one of wavelet interpolation and spline interpolation.

12. The method of claim 10, wherein the interpolation comprises an orthonormal expansion sampling method.

13. The method of claim 12, wherein the orthonormal expansion is selected from the group consisting of Legendre sampling, Tchebyshev sampling, and Sinc sampling.

14. The method of claim 10, further comprising varying interpolation in radial zones to increase a number of samples in a distal zone region with respect to the transducers.

15. An ultrasound probe, comprising:
   a probe housing;
   an array of piezoelectric transducers disposed in a transducer head detachable attached to the probe housing, wherein each piezoelectric transducer in the array includes a piezoelectric crystal;
   a beamformer disposed in the probe housing, the beamformer including beam forming and control electronics to shape a gain and a delay of voltage pulses coupled to the array of the piezoelectric transducers with a firing sequence in which a selection of active piezoelectric crystals is varied over time in a sequence selected to shift a spatial center of a transmitted ultrasound pulse over the firing sequence to achieve at least ½ piezoelectric transducer crystal physical resolution; and
   scan conversion electronics in the probe housing to convert detected reflected ultrasound pulses into ultrasound images.

16. The ultrasound probe of claim 15, wherein the firing sequence is selected to achieve ½ crystal physical resolution and interpolation is performed of detected reflected ultrasound pulses to achieve ¼ crystal digital resolution.

17. The ultrasound probe of claim 15, wherein the selection includes performing at least one of varying the number of piezoelectric crystals driven and shifting a position of piezoelectric crystals activated.

18. The ultrasound probe of claim 17, wherein the selection includes varying a number of active piezoelectric crystals over the firing sequence.

19. The ultrasound probe of claim 15, wherein the selection includes varying a spatial distribution of active piezoelectric crystals over the firing sequence.

20. The ultrasound probe of claim 19, wherein the scan conversion electronics applies a time varying focus coefficients for the detected ultrasound pulses to improve spatial focus.

21. The ultrasound probe of claim 15, wherein the selection comprising sequentially varying active piezoelectric crystals over the firing sequence to move the transmitted beam focal point by ½ crystal at a time so that the center of distribution of the pulse is shifted ½ crystal at a time in each firing sequence.

22. The ultrasound probe of claim 15, wherein the scan conversion electronics performs scan line conversion of data received from reflected ultrasound pulses, including performing, in a scan line domain, interpolation to increase a number of samples in scan line conversion.

23. The ultrasound probe of claim 22, wherein the scan conversion electronics performs interpolation to increase a number of samples in scan line conversion.

24. The ultrasound probe of claim 23, wherein the scan conversion electronics performs interpolation in radial zones to increase a number of samples in a distal zone region with respect to the transducers.

25. The ultrasound probe of claim 15, further comprising a calibration module to perform auto-calibration of the ultrasound probe.

26. An ultrasound probe, comprising,
a probe housing;
an array of piezoelectric transducers disposed in a transducer head detachably attached to the probe housing, wherein each piezoelectric transducer in the array includes a piezoelectric crystal;
beamforming means in the probe housing to shape a gain and a delay of voltage pulses coupled to the array of the piezoelectric transducers with a firing sequence in which a selection of active piezoelectric crystals is varied over time in a sequence selected to shift a spatial center of a transmitted ultrasound pulse over the firing sequence to achieve at least ½ piezoelectric transducer crystal physical resolution; and
scan conversion means in the probe housing including interpolation means to increase a number of samples in scan conversion.

27. A method of providing super-resolution in an ultrasound imaging system having a handheld probe including piezoelectric transducer having an array of piezoelectric crystals, comprising:
generating ultrasound pulses, including generating voltage pulses within the handheld probe in a firing sequence to drive the array of piezoelectric transducer crystals is selected such that a gain and a delay of each voltage pulse coupled to the array of piezoelectric transducer crystals splits the resolution to sub-pixel accuracy in which a selection of active piezoelectric crystals is varied over time in a sequence selected to shift a spatial center of a transmitted ultrasound pulse over the firing sequence to achieve at least ½ piezoelectric transducer crystal physical resolution;
detecting reflected ultrasound pulses;
performing scan conversion within the handheld probe for detected reflected ultrasound pulses, including performing, in a scan line domain, interpolation of samples for scan line processing used to reconstruct the ultrasound image; and
outputting ultrasound images.

28. The method of claim 27, wherein the interpolation comprises at least one of wavelet interpolation and spline interpolation.

29. The method of claim 27, wherein the interpolation comprises an orthonormal expansion sampling method.

30. The method of claim 29, wherein the orthonormal expansion is selected from the group consisting of Legendre sampling, Tchebyshev sampling, and Sinc sampling.

* * * * *